[12] United States Patent
Bilgic

(10) Patent No.: US 9,717,692 B2
(45) Date of Patent: Aug. 1, 2017

(54) EFFERVESCENT FORMULATIONS COMPRISING DEXKETOPROFEN

(71) Applicant: Mahmut Bilgic, Istanbul (TR)

(72) Inventor: Mahmut Bilgic, Istanbul (TR)

( * ) Notice: Subject to any disclaimer, the term of this patent is extended or adjusted under 35 U.S.C. 154(b) by 95 days.

(21) Appl. No.: 13/933,323

(22) Filed: Jul. 2, 2013

(65) Prior Publication Data
US 2014/0030326 A1    Jan. 30, 2014

Related U.S. Application Data

(63) Continuation-in-part of application No. PCT/TR2012/000085, filed on May 8, 2012, and a continuation-in-part of application No. PCT/TR2012/000083, filed on May 14, 2012.

(30) Foreign Application Priority Data

May 18, 2011 (TR) ............... a 2011 04864
Apr. 30, 2012 (TR) ............... a 2012 05008
May 8, 2012 (TR) ............... a 2012 05317

(51) Int. Cl.
A61K 31/192 (2006.01)
A61K 9/20 (2006.01)
A61K 9/46 (2006.01)
A61K 45/06 (2006.01)
A61K 31/133 (2006.01)
A61K 31/166 (2006.01)
A61K 31/197 (2006.01)
A61K 31/223 (2006.01)
A61K 31/704 (2006.01)

(52) U.S. Cl.
CPC .......... *A61K 9/2054* (2013.01); *A61K 9/0007* (2013.01); *A61K 9/2009* (2013.01); *A61K 9/2018* (2013.01); *A61K 31/133* (2013.01); *A61K 31/166* (2013.01); *A61K 31/192* (2013.01); *A61K 31/197* (2013.01); *A61K 31/223* (2013.01); *A61K 31/704* (2013.01); *A61K 45/06* (2013.01)

(58) Field of Classification Search
None
See application file for complete search history.

(56) References Cited

U.S. PATENT DOCUMENTS

2010/0204259 A1    8/2010    Tygesen et al.

FOREIGN PATENT DOCUMENTS

| EP | 0668851 A1 | 8/1995 | |
| JP | 2003306430 A | * 10/2003 | |
| WO | WO-94/11332 A1 | 5/1994 | |
| WO | WO 9410994 A1 | * 5/1994 | ........... A61K 9/0007 |
| WO | WO-02/098388 A2 | 12/2002 | |

OTHER PUBLICATIONS

Chivte, "Efficacy and Safety of Dexketoprofen Tablet in treatment of Acute Dental Pain in Indian Patients", JICDRO, vol. 1/Issue No. 2, pp. 85-90 (2009): retrieved from on-line website http://www.jicdro.org/downloadpdf.asp?issn=2231-0754;year=2009;volume=1;issue=2;spage=85;epage=90;aulast=Chivte;type=2 on Oct. 24, 2014).*
An Engliish translation of DEXMOL prescription information (XP-55042987, Dec. 20, 2010) and (2014, tranlated).*
Braga et al. "Crystal Polymorphism and Multiple Crystal Forms," Structure Bond (2009) 132: pp. 25-50.*
Morissette et al., "High-throughput crystallization: polymorphs, salts, co-crystals and solvates of pharmaceutical solids", Advanced Drug Delivery Reviews 56 (2004), 275-300.*
Vippagunta et al. "Crystalline solids", Advanced Drug Delievery Reviews 48 (2001) 3-26.*
Machine Translation of JP2003-306430 provided by Espacenet (last visit, Jun. 2, 2015).*
Sun et al. "Particle size specifications for solid oral dosage forms: A regulatory perspective", Review of American Pharmaceutical Business & Technology, 2010, pp. 1-10.*
International Search Report for International Application No. PCT/TR2012/000085, mailed Jan. 2, 2013 (6 pages).
International Search Report for International Application No. PCT/TR2012/000083, mailed Nov. 12, 2012 (4 pages).
Beetge et al., "The influence of the physicochemical characteristics and pharmacokinetic properties of selected NSAID's on their transdermal absorption," Intl J Pharm. 193(2):261-4 (2000).

* cited by examiner

*Primary Examiner* — Ernst V Arnold
*Assistant Examiner* — Kyung Sook Chang
(74) *Attorney, Agent, or Firm* — Clark & Elbing LLP

(57) ABSTRACT

The present invention relates to water-soluble formulations comprising the active agent dexketoprofen and to a process for production of said formulations. The present invention also relates to pharmaceutical formulations comprising dexketoprofen which is used in symptomatic treatment of mild to moderate pains such as musculoskeletal pains, dysmenorrhoea, toothache, post-operative pains. The formulations are characterized in being in effervescent form.

44 Claims, No Drawings

EFFERVESCENT FORMULATIONS COMPRISING DEXKETOPROFEN

CROSS-REFERENCE TO RELATED APPLICATIONS

This application is a continuation-in-part of PCT/TR2012/000085, filed May 8, 2012 and PCT/TR2012/000083, filed May 14, 2012, which are incorporated herein by reference in their entireties. This application is entitled to and claims priority benefits to application Ser. No.: TR2011/04864, filed May 18, 2011, TR2012/05008, filed Apr. 30, 2012, and TR2012/05317 filed May 8, 2012.

BACKGROUND OF THE INVENTION

The present invention relates to effervescent formulations which include the active substance dexketoprofen and which rapidly dissolve in water; and to a process for production of said effervescent formulations. The present invention also relates to pharmaceutical formulations including dexketoprofen which is used in symptomatic treatment of mild to moderate pains such as musculoskeletal pains, dysmenorrhoea, toothache, post-operative pains. Said formulations are characterized in being in effervescent form.

Dexketoprofen, named (+)-(S)-2-(3-Benzoylphenyl) propionic acid (Formula I), is the S (+) enantiomer of ketoprofen which is responsible for therapeutic effect. Nonetheless, it was disclosed that S (+) enantiomer of ketoprofen shows a quicker and stronger effect than racemic ketoprofen of the same amount (Sunshine et al., WO89/046558). Dexketoprofen or its pharmaceutically suitable salts are analgesic, anti-inflammatory, and antipyretic drugs belonging to the group of non-steroidal anti-inflammatory drugs.

Formula I

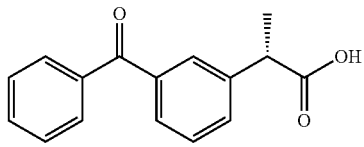

Dexketoprofen is produced by Menarini as dexketoprofen tromethamine salt under the tradename Keral on the market. Dexketoprofen tromethamine salt was first disclosed in the European patent numbered EP0668851. In addition, said patent also discloses the production method, suitable dosage forms and indications of dexketoprofen tromethamine salt.

Dexketoprofen and its pharmaceutically acceptable salts are drugs used as antipyretic, analgesic and anti-inflammatory in treatment of mild and moderate pains like toothache, menstrual pain, post-operative pains and musculoskeletal pains. In the treatment of the said pains, dexketoprofen is desired to reach to peak plasma concentration quickly in order to relieve these pains rapidly. It widely depends on absorption of dexketoprofen in the gastrointestinal system in a short time after it is taken into the body.

Dexketoprofen is found in forms of 50 mg/2 ml injection solution, 25 mg film tablet, and 25 mg effervescent tablet on the market.

In order for active agents which are taken in solid oral dosage forms such as capsule, conventional tablet or film tablet to be absorbed; firstly, the said substance must completely dissolve in gastric juice. Moreover, the gastric juice amount affects the dissolution rate of the active substance and therefore the absorption rate. In the case that gastric juice amount is low, the dissolution rate of the active substance and also the absorption rate is declined. Dissolution of an organic acid derivative substance such as dexketoprofen in the gastric fluid before being absorbed in the digestive system pulls pH of the stomach down even more and this not only affects the dissolution rate and therefore the absorption of dexketoprofen, but also causes stomach problems because of contact of the active agent with the stomach for too long. Low absorption of dexketoprofen caused by its failure to dissolve in an efficient amount leads to low bioavailability, resulting in failure to perform an effective treatment.

As seen, formulations which can allow dissolution of dexketoprofen independent from gastric fluid and pH are needed in order to perform an effective treatment.

From another aspect, there is need for new formulations which can provide high absorption of dexketoprofen by enabling complete dissolution of the active agent dexketoprofen and therefore can provide high bioavailability; and for dosage forms which include these formulations.

It has also been seen that the surface of water turns yellow when effervescent formulations comprising dexketoprofen contact with water during its use and yellowing on water surface affects patients negatively during use of the drug. It has been observed that stability problems of said dexketoprofen formulations cause negative results such as yellowing on water surface during use as mentioned or some part of the drug comprising active agent is not dissolved. In that case, the patient can say that the treatment could not be provided effectively due to the problems observed during the use of effervescent formulations comprising dexketoprofen such as yellow formation in water and sediments of the drug which is not dissolved.

Accordingly, there is need to develop stable effervescent formulations which do not present problems in the prior art such as yellowing in water, remaining of some part of the active agent without dissolving and, in line with this, sedimentation of the drug on the bottom of the glass.

SUMMARY OF THE INVENTION

The invention features a formulation including dexketoprofen or a pharmaceutically acceptable salt thereof characterized in that the formulation is in water-soluble form.

In one aspect, dexketoprofen in the formulation is in the form of a pharmaceutically acceptable solvate, hydrate, salt, amorphous, and/or crystalline form thereof. In some embodiments, dexketoprofen is in the form of trometamol salt. The formulation can be, e.g., in the form of water-soluble powder, water-soluble granule, water-soluble tablet, effervescent powder, effervescent granule, or effervescent tablet. In some embodiments, the amount of dexketoprofen is in the range of 1 mg to 250 mg (e.g., 5 mg to 100 mg). Also in some embodiments, the formulation includes dexketoprofen having d90 value in the range of 250-600 μm (e.g., 300-500 μm or 350-450).

In some embodiments, the formulation further includes other pharmaceutically acceptable excipients along with dexketoprofen, e.g., as binder, carrier, sweetener and/or taste regulating agent, coloring agent or flavoring agent, filling agents, lubricants, glidant, viscosity enhancers, anti-foam agents, surfactants, diluents, and optionally an effervescent couple including one effervescent acid and one effervescent base.

In some embodiments, the binder is selected from a group including povidone, cellulose ester, sucrose, lactose, cellulose derivatives, sorbitol and/or mannitol. The average particle size of sorbitol and/or mannitol can be, e.g., in the range of 100-450 μm, 150-400 μm, or 200-350 μm. When in water soluble tablet or effervescent tablet form, the formulation can have, e.g., a hardness value of 8 kP and/or the form disintegrates within 1-2.5 minutes.

In all aspects of the invention, the formulation can include, e.g., dexketoprofen or a pharmaceutically acceptable salt thereof, in the range of 1-15%, binder in the range of 1-10%, filling agent in the range of 2-25%, sweetener and/or taste regulating agent in the range of 0.1-10%, coloring, and/or flavoring agent in the range of 0.5-8%, diluent in the range of 0-65%, and effervescent couple in the range of 0-90% in proportion to the total weight of unit dose amount.

The invention also features a method for preparing water-soluble formulations as described above wherein the method uses wet and/or granulation techniques.

The invention further features a formulation in effervescent form including, e.g., dexketoprofen, or a pharmaceutically acceptable salt thereof, at least one acidic agent, at least one basic agent, binder, and optionally other excipients, characterized in that the formulation includes at least one acid salt as an acidic agent.

In one aspect of the above invention, dexketoprofen in the formulation is in form of an organic salt (e.g., a trometamol salt).

The formulation can, e.g., include dexketoprofen in the range of 0.5-30%, 1-25%, or 2-20% of total formulation by weight in proportion to unit formulation. In some embodiments, the acidic agent used in the formulation is selected from the group consisting of monosodium citrate, calcium phosphate, sodium phosphate, sodium acetate, dibasic sodium phosphate, tribasic sodium citrate, monobasic sodium phosphate, sodium acid pyrophosphate, sodium acid sulphite, and combinations thereof. The basic agent used in the formulation can be, e.g., selected from the group consisting of potassium carbonate, potassium bicarbonate, potassium citrate, potassium hydroxide, sodium carbonate, sodium hydrogen carbonate, sodium hydrogen citrate, and combinations thereof. The binder used in the formulation can be, e.g., selected from the group consisting of ethyl cellulose, gelatine, hydroxyethyl cellulose, hydroxymethyl cellulose, hydroxypropyl cellulose, hypromellose, magnesium aluminium silicate, methyl cellulose, povidone, sorbitol powder, and combinations thereof. For example, the dexketoprofen:binder in the formulation is in the range of 5:1 to 1:5 or 4:1 to 1:3.

In all aspects of the above invention, effervescent formulations can include, e.g., an effervescent tablet, effervescent granule, or effervescent powder.

The formulation optionally includes at least one pharmaceutically acceptable excipient used together with dexketoprofen or a pharmaceutically acceptable salt thereof, acidic agent, basic agent, and binder. In certain embodiments, the pharmaceutically acceptable excipients optionally used together with dexketoprofen or a pharmaceutically acceptable salt thereof, include an acidic agent, basic agent and binder are selected from a group including filling agent, sweetener and/or taste regulating agent, flavoring agent, and/or lubricant.

The formulation can optionally include a second active agent in addition to dexketoprofen. In some embodiments, the second active agent used together with dexketoprofen is selected from analgesic, antipyretic, muscle relaxant, non-steroidal anti-inflammatory agents, or combinations thereof. In another preferred embodiment, paracetamol, thiocolchicoside, a mucolytic drug, acetyl cysteine, or diclofenac is used as the second active agent in addition to dexketoprofen.

The formulation according to the above invention can be, e.g., characterized in that the formulation includes analgesic, antipyretic, muscle relaxant, and non-steroidal anti-inflammatory agents, which can be used as the second active agent in the range of 1% to 40% in proportion to total weight of the unit dose. The formulation can include, e.g., an acidic agent in the range of 30-70%, a basic agent in the range of 20-50%, a filling agent in the range of 1-25%, a binder in the range of 0.5-20%, a sweetener and/or taste regulating agent in the range of 0.1-10%, a flavoring agent in the range of 1-15%, and/or a lubricant in the range of 0.1-1.5% in proportion to total weight of the unit dose.

The invention also features a method of preparing any of the above formulations including, e.g., the steps of: mixing the acidic agent, basic agent, optionally taste regulating agent and, if available, the second active agent used together with dexketoprofen, granulating the mixture with a granulation solution including binder; drying and sieving the granules obtained, mixing with the active agent dexketoprofen, sweetener(s), optionally filling agent or lubricant and flavoring agent, and producing tablets by loading the final mixture to the tablet compression machine and blistering them or filling them in sachets.

DESCRIPTION OF THE INVENTION

Surprisingly, the inventors have brought solutions for the problems experienced in solid oral dosage forms in the prior art by developing water-soluble formulations comprising dexketoprofen and dosage forms comprising thereof.

Accordingly, the present invention relates to water-soluble formulations comprising dexketoprofen or a pharmaceutically acceptable salt thereof and preparation methods of these. Surprisingly, the developed water soluble formulation comprising dexketoprofen or a pharmaceutically acceptable salt thereof has enabled dexketoprofen to dissolve in water completely before taken into the body; in line with this, it has been observed that the absorption and bioavailability have increased. Therefore, the water soluble formulation comprising dexketoprofen developed has provided that an effective amount of dexketoprofen is taken by the patient and an effective treatment is carried out.

The first aspect of the present invention is water soluble formulations comprising dexketoprofen.

When compared to solid oral dosage forms, water-soluble dexketoprofen formulations have been observed to be more advantageous than other oral dosage forms comprising dexketoprofen in terms of enabling an effective amount of the active substance dexketoprofen to dissolve and be absorbed. The developed water-soluble formulations comprising dexketoprofen have provided that problems observed in solid oral dosage forms in the prior art are solved by enabling dexketoprofen to dissolve in water and become ready to be absorbed before taken into the body and an effective treatment is realized when dexketoprofen reaches its peak plasma concentration.

Water-soluble formulation of the present invention comprises dexketoprofen as the active substance. The term "dexketoprofen" used here includes the free acid, as well as pharmaceutically acceptable salts, solvates, hydrates, amorphous and crystalline forms of dexketoprofen. Effervescent formulation of the present invention preferably comprises a pharmaceutically acceptable salt of dexketoprofen, preferably trometamol salt thereof.

Another aspect of the invention is water-soluble formulations comprising dexketoprofen trometamol.

The amount of the active agent comprised in the water-soluble formulations of the present invention is in the range of 1 mg to 250 mg, preferably in the range of 5 mg to 100 mg.

In another aspect, the present invention relates to water soluble formulations comprising dexketoprofen in the range of 1 mg to 250 mg, preferably in the range of 5 mg to 100 mg.

Water-soluble formulations can be in water-soluble powder, water-soluble granule, water-soluble tablet, effervescent powder, effervescent granule or effervescent tablet form. In the case that the formulation of the present invention is in the form of water soluble tablet or effervescent tablet, hardness and thus disintegration time are important parameters for the bioavailability of the active agent and efficiency of the treatment. The inventors have found that the particle size of dexketoprofen used as active agent in the formulation has a great influence on the disintegration time and the absorption and thus bioavailability of dexketoprofen. When the formulation of the present invention comprise dexketoprofen active agent having d90 value in the range of 250-600 μm, preferably 300-500 μm, more preferably 350-450 μm, said formulation can dissolve in water quickly and effective amount of dexketoprofen can be absorbed easily therefore an efficient treatment can be provided.

In another aspect, the present invention relates to water soluble formulations wherein said formulations are in water soluble tablet or effervescent tablet form, said formulations comprise dexketoprofen having d90 value in the range of 250-600 μm, preferably 300-500 μm, more preferably 350-450 μm. The expression of "d90 value" means that 90% of dexketoprofen used as active agent by volume has particle size below this value and 10% of dexketoprofen by volume has particle size above this value.

Table 1 indicates data of dissolution time of the effervescent tablet of the present invention so that 98.7% of dexketoprofen active agent can be dissolved in water. The dissolution data have been recorded based on the change in d90 value of dexketoprofen used as active agent. According to the specifications, the dissolution time of said effervescent tablets of the present invention should be maximum 5 minutes. The results clearly show that the effervescent tablet can dissolve within this range in the case that the formulation of the present invention comprises dexketoprofen having d90 value in the range of 250-600 μm. In fact, it can easily be seen that the preferable range of the d90 value of dexketoprofen is 300-500 μm and the most preferable one is 350-450 μm for achieving optimum dissolution time of the obtained effervescent tablet. Therefore, it can be concluded that the effervescent tablets of the present invention, in which dexketoprofen having d90 value in the range of 250-600 μm, preferably 300-500 μm, more preferably 350-450 μm is used, are much preferred via its optimum dissolution time in water.

TABLE 1

The dissolution times varying depending on d90 values of dexketoprofen

| D90 Value of Dexketoprofen (μm) | Dissolution Time (min) |
|---|---|
| 50 | 5.7 |
| 100 | 6.1 |
| 150 | 5.7 |

TABLE 1-continued

The dissolution times varying depending on d90 values of dexketoprofen

| D90 Value of Dexketoprofen (μm) | Dissolution Time (min) |
|---|---|
| 200 | 5.2 |
| 250 | 4.9 |
| 300 | 3.5 |
| 350 | 2.9 |
| 400 | 1.8 |
| 450 | 2.4 |
| 500 | 3.7 |
| 550 | 4.2 |
| 600 | 5.1 |
| 650 | 5.7 |
| 700 | 6.3 |

Water-soluble formulations of the present invention can also comprise other pharmaceutically acceptable excipients along with dexketoprofen.

Water-soluble formulations of the invention can also comprise excipients such as binder, optionally an effervescent couple comprising effervescent acid and effervescent base, carrier, sweetener and/or taste regulating agent, coloring or flavoring agent, filling agents, lubricants, glidants, viscosity enhancers, anti-foaming agents, surfactants along with dexketoprofen.

The binder which is used in water-soluble formulations of the present invention is selected from, but not limited to, a group comprising povidone, cellulose ester, sucrose, lactose, cellulose derivatives, sorbitol and/or mannitol.

Tablet hardness should also be taken into consideration in terms of the bioavailability of active agent and thus the efficiency of the treatment. Because, tablets with high hardness value leads to a slow dispersion and dissolution. Therefore, sufficient active agent cannot be dissolved and thus bioavailibity of dexketoprofen decreases. Based on the studies, the inventors have seen that the particle size and the material of the excipient are important parameters on optimizing the tablet hardness and achieving high bioavailibity of dexketoprofen.

The inventors have observed that when the formulation of the present invention comprise sorbitol and/or mannitol as binder and the average particle size of the sorbitol and/or mannitol is in the range of 100-450 μm, preferably 150-400 μm, more preferably 200-350 μm, the hardness of the tablets has been found as 8 kP, which is an optimum hardness value within specification limits. Therefore, the water soluble and/or effervescent tablets can disintegrate within 1-2.5 minutes when they contact with water. Accordingly, when the formulation dissolve in water quickly and easily, the absorption and the bioavailability of dexketoprofen used as active agent can increase and hence an effective treatment can be provided.

In another aspect, the present invention relates to water soluble formulations wherein
said formulations are in water soluble tablet or effervescent tablet form,
said formulations comprise sorbitol and/or mannitol as binder, and
the average particle size of sorbitol and/or mannitol is in the range of 100-450 μm, preferably 150-400 μm, more preferably 200-350 μm.

Based on the study on the effect of average particle size of sorbitol used as binder on the hardness and dissolution time of the effervescent tablets comprising dexketoprofen, the inventors have observed that sorbitol should have an average particle size in an optimum range in order to achieve rapid dissolution and efficient treatment. The dissolution time is tested for achieving dissolution of 98.7% dexketoprofen active agent in water. According to the specifications, the hardness value of the tablet should be in the range of 6-9 kP and the optimum range of the dissolution time for said effervescent tablet is maximum 5 minutes. Therefore, it can clearly be seen that when sorbitol having average particle size in the range of 100-450 μm is used as binder, the optimum hardness and dissolution time values which are within the given specification limits can be achieved. The preferable range is obtained as 150-400 μm and the most preferable range is obtained as 200-350 μm. It can be seen that when sorbitol having average particle size in the most preferable range of 200-350 μm, the hardness of the tablet is about 7-8 kP and the dissolution time is about 2 minutes which are the most suitable values for obtaining a high dissolution and bioavailability. Hence, it can be concluded that the effervescent tablets of the present invention, in which sorbitol having average particle size in the range of 100-450 μm, preferably 150-400 μm, more preferably 200-350 μm, are much preferred via its optimum hardness and dissolution time.

TABLE 2

The hardness and dissolution times varying depending on average particle size values of sortibol

| Average Particle Size of Sorbitol (μm.) | Hardness (kP) | Dissolution Time (min) |
| --- | --- | --- |
| 50 | 5.2 | 1.1 |
| 100 | 6.1 | 1.5 |
| 150 | 6.4 | 1.8 |
| 200 | 7.2 | 2.2 |
| 250 | 7.5 | 2.5 |
| 300 | 8.1 | 1.9 |
| 350 | 8.8 | 2.8 |
| 400 | 8.5 | 3.3 |
| 450 | 9.1 | 3.8 |
| 500 | 9.4 | 5.2 |
| 550 | 9.8 | 5.4 |
| 600 | 10.1 | 5.8 |

Carriers which can be used in water-soluble formulations of the present invention can be selected from, but not limited to, a group comprising lactose, saccharose, sorbite, mannitol, starch, pectin and cellulose.

Filling agents which can be used in water-soluble formulations of the present invention can be selected from a group comprising cyclodextrin, maltodextrin, ethyl cellulose, lactose, sucrose, glucose, cellulose, microcrystalline cellulose, calcium carbonate, magnesium carbonate, starch and talc.

Sweeteners and/or taste regulating agents which can be used in water-soluble formulations of the present invention can be selected from a group comprising sucralose, sucrose, fructose, glucose, galactose, xylose, dextrose, laevulose, lactose, maltose, maltodextrin, mannitol, maltitol, maltol, sorbitol, xylitol, erythritol, lactitol, isomalt, corn syrup, saccharin, saccharin salts, acesulfame potassium, aspartame, acesulfame potassium and cyclamates or a combination thereof.

Effervescent acids which can be used in water-soluble formulations of the present invention can be selected from a group comprising food acids such as citric acid, tartaric acid, ascorbic acid, malic acid, fumaric acid, adipic and succinic acid, acetyl salicylic acid; acid salts like sodium dihydrogen phosphate, sodium acid pyrophosphate, acid citrate salts, amino acid hydrochlorides, sodium acid sulphite; their hydrates and anhydrates and combinations thereof.

Effervescent bases which can be used in water-soluble formulations of the present invention can be selected from a group comprising carbonate and bicarbonate salts such as sodium bicarbonate, sodium carbonate, potassium bicarbonate, potassium carbonate, sodium sesquicarbonate, sodium glycine carbonate, L-lysine carbonate, arginine carbonate, amorphous calcium carbonate, calcium carbonate and combinations thereof.

Diluents which can be used in water-soluble formulations of the present invention can be selected from a group comprising calcium carbonate, calcium sulphate, dibasic calcium sulphate, dibasic calcium phosphate, tribasic calcium phosphate, calcium phosphate, microcrystalline cellulose, magnesium carbonate, magnesium oxide, sodium chloride, xylitol, lactose, maltose, dextrin, maltodextrin, mannitol, sorbitol, starch or combinations thereof.

Water soluble formulations of the invention can comprise dexketoprofen or a pharmaceutically acceptable salt thereof in the range of 1-15%, binder in the range of 1-10%, filling agent in the range of 2-25%, sweetener and/or taste regulating agent in the range of 0.1-10%, colouring and/or flavoring agent in the range of 0.5-8%, diluent in the range of 0-65% and effervescent couple in the range of 0-90% when compared to the total weight of unit dose amount.

The inventors have also surprisingly observed that an effervescent formulation comprising dexketoprofen or a pharmaceutically acceptable salt thereof, at least one acidic agent, at least one basic agent, binder and optionally other excipients does not cause any yellowing in water or sedimentation of the drug and is rather stable in the case that said formulation comprises at least one acidic salt as acidic agent.

Accordingly, another aspect of the invention is a process for preparing water-soluble formulations of the present invention comprising dexketoprofen by using wet and/or dry granulation techniques available in the prior art.

The present invention also relates to effervescent formulations comprising;
dexketoprofen or a pharmaceutically acceptable salt thereof
at least one acidic agent
at least one basic agent
binder, and
optionally other excipients
and is characterized in comprising at least one acid salt as acidic agent.

A characteristic of formulations of the invention is that dexketoprofen in said formulations is preferably in form of organic salts, more preferably in form of trometamol salt. Another characteristic of the formulations of the invention is that dexketoprofen is in the range of 0.5-30%, preferably in the range of 1-25%, more preferably in the range of 2-20% by weight in proportion to unit formulation.

The acidic agent that will be used in formulations of the invention can be selected from a group comprising monosodium citrate, calcium phosphate, sodium phosphate, sodium acetate, dibasic sodium phosphate, tribasic sodium citrate, monobasic sodium phosphate, sodium acid pyrophosphate and sodium acid sulphite or combinations thereof. Preferably, monosodium citrate can be used as acidic agent in effervescent formulations prepared according to the invention.

In another aspect, effervescent formulations of the invention can comprise effervescent tablet, effervescent granule and effervescent powders.

Formulations prepared according to the present invention can preferably be formulated in effervescent tablet form.

The basic agent in formulations of the invention can be selected from a group comprising potassium carbonate, potassium bicarbonate, potassium citrate, potassium hydroxide, sodium carbonate, sodium hydrogen carbonate, sodium hydrogen citrate or a combination thereof. Preferably, sodium hydrogen carbonate can be used as basic agent in formulations of the invention.

The binder used in formulations of the present invention can be selected from a group comprising ethyl cellulose, gelatine, hydroxyethyl cellulose, hydroxymethyl cellulose, hydroxypropyl cellulose, hypromellose, magnesium aluminium silicate, methylcellulose, povidone, sorbitol powder or a combination thereof.

Preferably, sorbitol powder can be used as binder in formulations of the invention.

As mentioned before, stability problem of effervescent formulations comprising dexketoprofen caused yellowing in water and sedimentation of some part of the drug without dissolving. Inventors have observed that desired stability is obtained in the case that the ratio of dexketoprofen:binder in formulations of the invention is in the range of 5:1 to 1:5, preferably in the range of 4:1 to 1:3 by weight.

Another characteristic of the formulations of the invention is that said formulations optionally comprise at least one pharmaceutically acceptable excipient which will be used together with dexketoprofen or a pharmaceutically acceptable salt of it, acidic agent, basic agent and binder.

Accordingly, another characteristic of the formulations of the invention is that pharmaceutically acceptable excipients which can optionally be used together with dexketoprofen or a pharmaceutically acceptable salt of it, acidic agent, basic agent and binder can be selected from a group comprising filling agent, sweetener and/or taste regulating agent, flavoring agent and lubricant.

Taste of the drug poses another problem in addition to the ones such as yellowing in water and sedimentation of the drug in effervescent formulations comprising dexketoprofen. Sweeteners are used in order to prevent this situation which affects the patient negatively during use. The inventors have observed that using a composition comprising two different sweeteners in formulations prepared according to the invention solves the problem of taste of the drug.

Accordingly, another characteristic of formulations of the invention is that a composition comprising two different sweeteners is used as sweetener and/or taste regulating agent.

Sweeteners and/or taste regulating agents used in formulations of the present invention can be selected from a group comprising acesulfame potassium, aspartame, fructose, maltitol, xylitol, saccharine sodium cyclamate, sucralose, sucrose, sodium chloride, trehalose, dextrose, maltose, and mannitol.

In another aspect, the sweetener and/or taste regulating agent composition used as sweetener in formulations of the invention can preferably comprise acesulfame potassium and aspartame.

The filling agent that can be used in formulations prepared according to the invention can be selected from a group comprising D-mannitol, xylitol, microcrystalline, crospovidone, dibasic calcium phosphate anhydrous, lactose, starch, maltose, dextrin, maltodextrin, magnesium carbonate, talc or a combination thereof.

The flavoring agent that can be used in formulations of the invention can be selected from flavors such as menthol, menthane, anethole, methyl salicylate, eucalyptol, cinnamon, 1-methyl acetate, sage, eugenol, oxanone, lemon, orange, strawberry, blackberry or a combination thereof.

Preferably, lemon flavor can be used as flavoring agent in formulations of the invention. The lubricants used in formulations of the present invention can be selected from a group comprising talc, magnesium stearate, PEG 6000, silicon dioxide, sodium benzoate, potassium benzoate, stearic acid, sodium stearyl fumarate and/or a combination thereof.

Optionally, a second active agent can be used in effervescent formulations comprising dexketoprofen according to the present invention together with dexketoprofen.

Accordingly, the second active agent that can be used in formulations of the invention together with dexketoprofen can be selected from analgesic, antipyretic, muscle relaxant, non-steroidal anti-inflammatory agents or a combination thereof.

Preferably, an analgesic and/or antipyretic agent, more preferably paracetamol can be used in dexketoprofen effervescent formulations of the present invention as the optional second active agent together with dexketoprofen.

Preferably, a muscle relaxant, more preferably thiocolchicoside can be used in dexketoprofen effervescent formulations of the present invention as the optional second active agent in addition to dexketoprofen.

Preferably, a mucolytic drug, more preferably acetylcysteine, can be used in dexketoprofen effervescent formulations of the present invention as the optional second active agent together with dexketoprofen.

Preferably, a non-steroidal anti-inflammatory agent, more preferably diclofenac, can be used in dexketoprofen effervescent formulations of the present invention as the optional second active agent together with dexketoprofen.

Another characteristic of the formulations according to the invention is that said formulations comprise analgesic, antipyretic, muscle relaxant and non-steroidal anti-inflammatory agents which can be used as the second active agent in the range of 1% to 40% by weight in proportion to total weight of the unit dose.

The formulations prepared according to the present invention comprise acidic agent in the range of 30-70%, basic agent in the range of 20-50%, filling agent in the range of 1-25%, binder in the range of 0.5-20%, sweetener and/or taste regulating agent in the range of 0.1-10%, flavoring agent in the range of 1-15%, lubricant in the range of 0.1-1.5% in proportion to total weight of the unit dose.

The pharmaceutical formulation of the invention can be prepared by a method comprising;
- mixing the acidic agent, basic agent, binder, optionally taste regulating agent and, if available, the second active agent used in addition to dexketoprofen,
- granulating the mixture with a granulation solution comprising binder; drying and sieving the granules obtained,
- mixing them with the active agent dexketoprofen, sweetener(s), optionally filling agent or lubricant and flavoring agent,
- producing tablets by loading the final mixture to the tablet compression machine and blistering them or filling them in sachets.

The pharmaceutical formulation of the invention can be used in symptomatic treatment of mild to moderate pains such as musculoskeletal pains, dysmenorrhoea, toothache, post-operative pains.

EXAMPLES

The examples below are given for a better explanation of the invention, yet the present invention should not be limited to these examples.

Example 1

Effervescent powder or granule comprising dexketoprofen

| Formulation Content | Amount (%) |
|---|---|
| Dexketoprofen Trometamol | 5.5 |
| Effervescent base | 35.5 |
| Effervescent acid | 42 |
| Binder | 3.5 |
| Filling agent | 7.5 |
| Sweetener | 3.5 |
| Flavouring agent | 2.5 |

The process for preparing the effervescent powder or granule dosage forms comprising dexketoprofen trometamol of the present invention comprises the steps of granulating the effervescent couple with a granulation solution comprising binder; drying and sieving the obtained granules; adding dexketoprofen trometamol, filling agent, sweetener and flavouring agent to the mixture.

Example 2

Effervescent tablet comprising dexketoprofen

| Formulation Content | Amount (%) |
|---|---|
| Dexketoprofen Trometamol | 15 |
| Binder | 6 |
| Filling agent | 21 |
| Diluent | 53 |
| Sweetener | 3 |
| Flavoring agent | 2 |

The process followed for preparing the water-soluble tablet dosage forms comprising dexketoprofen trometamol of the invention comprises the steps of dry mixing dexketoprofen trometamol, binder, filling agent, diluent, sweetener, flavouring agents; and compressing the final mixture obtained in tablet form in tablet compression machine.

Example 3

Effervescent tablet formulation comprising dexketoprofen

| Component name | % of amount in unit dose |
|---|---|
| Dexketoprofen Trometamol | 4 |
| Acidic agent | 40 |
| Basic agent | 31.5 |
| Filling agent | 12 |
| Binder | 8 |
| Sweetener 1 | 1.5 |
| Sweetener 2 | 1 |
| Flavor | 2 |

The formulation given above is prepared by wet-granulation method. Acidic agent, basic agent, effervescent base and binder are mixed and granulated with a granulation solution comprising binder. Granules which are dried and sieved are mixed with dexketoprofen trometamol, filling agent, sweeteners and flavoring agent. The composition is taken to tablet compression. Tablets are blistered and packaged.

Example 4

Effervescent tablet formulation comprising dexketoprofen and paracetamol

| Component name | % of amount in unit dose |
|---|---|
| Dexketoprofen Trometamol | 4 |
| Paracetamol | 19 |
| Acidic agent | 40 |
| Basic agent | 28.1 |
| Binder | 4 |
| Aroma regulator | 2 |
| Lubricant | 0.5 |
| Sweetener | 0.7 |
| Flavor | 1.7 |

The formulation given above is prepared by wet-granulation method. Paracetamol, acidic agent, basic agent, binder and taste regulating agent are mixed and granulated with a granulation solution comprising binder. Granules which are dried and sieved are mixed with dexketoprofen trometamol, lubricant, sweeteners and a flavoring agent. The composition is taken to tablet compression. Tablets are blistered and packaged.

What is claimed is:

1. A formulation comprising dexketoprofen or a pharmaceutically acceptable hydrate, salt, or amorphous form thereof and a binder, characterized in that said formulation is in water-soluble form, wherein the formulation comprises dexketoprofen having a d90 value in the range of 250-600 µm and wherein the ratio of dexketoprofen:binder in the formulation is in the range of 5:1 to 1:5 by weight.

2. The formulation according to claim 1, wherein the dexketoprofen is in the form of trometamol salt.

3. The formulation according to claim 1, wherein the water-soluble form is selected from the group consisting of a water-soluble powder, a water-soluble granule, a water-soluble tablet, an effervescent powder, an effervescent granule, and an effervescent tablet.

4. The formulation according to claim 1, wherein the amount of dexketoprofen is in the range of 1 mg to 250 mg.

5. The formulation according to claim 1, wherein the formulation comprises dexketoprofen having a d90 value in the range of 300-500 µm.

6. The formulation according to claim 1, wherein the formulation is in water soluble tablet or effervescent tablet form.

7. The formulation according to claim 1, wherein the formulation further comprises one or more pharmaceutically acceptable excipients selected from the group consisting of a carrier, a sweetener, a taste regulating agent, a colouring agent, a flavouring agent, a filing agent, a lubricant, a glidant, a viscosity enhancer, an anti-foam agent, a surfactant, a diluent, and an effervescent couple.

8. The formulation according to claim 7, wherein the effervescent couple comprises one effervescent acid and one effervescent base.

9. The formulation according to claim 1, wherein the binder is selected from a group consisting of povidone, cellulose ester, sucrose, lactose, cellulose derivatives, and sorbitol and/or mannitol.

10. The formulation according to claim 9, wherein the average particle size of the sorbitol and/or mannitol is in the range of 100-450 µm.

11. The formulation according to claim 1, wherein the formulation is in water soluble tablet or effervescent tablet form, wherein the formulation comprises sorbitol and/or mannitol as the binder, and wherein the average particle size of the sorbitol and/mannitol is in the range of 100-450 µm.

12. The formulation according to claim 11, wherein the water soluble tablet or effervescent tablet form has a hardness value of 8 kP or wherein the water soluble tablet or effervescent tablet form disintegrates within 1-2.5 minutes upon contact with water or an aqueous solution.

13. The formulation according to claim 1, wherein said formulation comprises dexketoprofen or a pharmaceutically acceptable salt thereof in the range of 1-15%, a binder in the range of 1-10%, a filling agent in the range of 2-25%, a sweetener and/or taste regulating agent in the range of 0.1-10%, a colouring and/or flavoring agent in the range of 0.5-8%, a diluent in the range of 0-65%, and an effervescent couple in the range of 0-90% in proportion to the total weight of a unit dose amount.

14. A method for preparing the water-soluble formulation according to claim 1, wherein said method uses wet and/or granulation techniques.

15. The formulation according to claim 1, wherein said formulation is an effervescent formulation comprising at least one acidic agent and at least one basic agent, wherein the at least one acidic agent is an acid salt.

16. The formulation according to claim 15, wherein the dexketoprofen is in the form of trometamol salt.

17. The formulation according to claim 15, wherein said formulation comprises dexketoprofen in the range of 0.5-30% of total formulation by weight in proportion to unit formulation.

18. The formulation according to claim 15, wherein the acid salt is selected from the group consisting of monosodium citrate, calcium phosphate, sodium phosphate, sodium acetate, dibasic sodium phosphate, tribasic sodium citrate, monobasic sodium phosphate, sodium acid pyrophosphate, sodium acid sulphite, and combinations thereof.

19. The formulation according to claim 18, wherein the acid salt is monosodium citrate.

20. The formulation according to claim 15, wherein the effervescent formulation is an effervescent tablet, an effervescent granule, or an effervescent powder.

21. The formulation according to claim 20, wherein the effervescent formulation is an effervescent tablet.

22. The formulation according to claim 15, wherein the at least one basic agent is selected from the group consisting of potassium carbonate, potassium bicarbonate, potassium citrate, potassium hydroxide, sodium carbonate, sodium hydrogen carbonate, sodium hydrogen citrate, and combinations thereof.

23. The formulation according to claim 22, wherein the basic agent is sodium hydrogen carbonate is used as basic agent in said formulation.

24. The formulation according to claim 15, characterized in that the binder used in said formulation is selected from the group consisting of ethyl cellulose, gelatine, hydroxyethyl cellulose, hydroxymethyl cellulose, hydroxypropyl cellulose, hypromellose, magnesium aluminium silicate, methyl cellulose, povidone, sorbitol powder, and combinations thereof.

25. The formulation according claim 15, further comprising a second active agent in addition to dexketoprofen.

26. The formulation according to claim 25, wherein the second active agent is selected from the group consisting of an analgesic, an antipyretic, a muscle relaxant, a mucolytic drug, and a non-steroidal anti-inflammatory agents.

27. The formulation according to claim 26, wherein the second active agent is an analgesic and wherein the analgesic is paracetamol.

28. The formulation according to claim 26, wherein the second active agent is a muscle relaxant and wherein the muscle relaxant is thiocolchicoside.

29. The formulation according to claim 26, wherein the second active agent is a mucolytic drug and wherein the mucolytic drug is acetyl cysteine.

30. The formulation according to claim 26, wherein the second active agent is a non-steroidal anti-inflammatory agent and wherein the non-steroidal anti-inflammatory agent is diclofenac.

31. The formulation according to claim 26, wherein the second active agent is in the range of 1% to 40% in proportion to total weight of the unit dose.

32. The formulation according to claim 15, wherein the formulation comprises an acidic agent in the range of 30-70%, a basic agent in the range of 20-50%, a filling agent in the range of 1-25%, a binder in the range of 0.5-20%, a sweetener and/or taste regulating agent in the range of 0.1-10%, a flavouring agent in the range of 1-15%, and a lubricant in the range of 0.1-1.5% in proportion to total weight of the unit dose.

33. The formulation according to claim 15, wherein the formulation is prepared by the steps of:
   (a) mixing the at least one acidic agent and at least one basic agent together with dexketoprofen,
   (b) granulating the mixture with a granulation solution comprising the binder;
   (c) drying and sieving the granules obtained, and
   (d) producing tablets by loading the final mixture to a tablet compression machine and blistering or filling the tablets in sachets.

34. The formulation according to claim 17, wherein said formulation comprises dexketoprofen in the range 1-25% of total formulation by weight in proportion to unit formulation.

35. The formulation according to claim 34, wherein said formulation comprises dexketoprofen in the range of 2-20% of total formulation by weight in proportion to unit formulation.

36. The formulation according to claim 4, wherein the amount of dexketoprofen is in the range of 5 mg to 100 mg.

37. The formulation according to claim 1, wherein the formulation comprises dexketoprofen having a d90 value in the range of 350-450 µm.

38. The formulation according to claim 10, wherein the average particle size of the sorbitol and/or mannitol is in the range of 150-400 µm.

39. The formulation according to claim 38, wherein the average particle size of the sorbitol and/or mannitol is in the range of 200-350 µm.

40. The formulation according to claim 1, wherein the ratio of dexketoprofen:binder in the formulation is in the range of 4:1 to 1:3 by weight.

41. The formulation according to claim 1, wherein the formulation allows for optimum dissolution time and stability of the dexketoprofen in water resulting in high absorption and bioavailability.

42. The formulation according to claim 41, wherein the optimum dissolution time is a maximum of 5 minutes.

43. The formulation according to claim 42, wherein the optimum dissolution time is within 1-2.5 minutes.

44. The formulation of claim 41, wherein the stability of the dexketoprofen in water is assessed by a decrease in sedimentation or discoloration of dexketoprofen in solution.

* * * * *